United States Patent [19]
Liddell et al.

[11] Patent Number: 5,952,460
[45] Date of Patent: Sep. 14, 1999

[54] PROCESS OF RECOVERING POLYMERS OF HYDROXYALKANOIC ACIDS

[75] Inventors: John MacDonald Liddell, Cleveland; Neil George, Leeds; Alan Hall, Huddersfield, all of United Kingdom

[73] Assignee: Monsanto Company, St. Louis, Mo.

[21] Appl. No.: 08/793,019

[22] PCT Filed: Aug. 15, 1995

[86] PCT No.: PCT/GB95/01925

§ 371 Date: Jul. 7, 1997

§ 102(e) Date: Jul. 7, 1997

[87] PCT Pub. No.: WO96/06178

PCT Pub. Date: Feb. 29, 1996

[30] Foreign Application Priority Data

Aug. 18, 1994 [GB] United Kingdom .................... 9416691
Feb. 16, 1995 [GB] United Kingdom .................... 9502980

[51] Int. Cl.⁶ ............................ C08G 63/89; C08G 63/06
[52] U.S. Cl. ............................ 528/503; 528/361; 528/481; 528/487; 528/490; 528/499; 528/502 F; 435/135; 435/136; 435/146
[58] Field of Search ...................... 528/361, 481, 528/499, 502 F, 503, 487, 490; 435/135, 136, 146

[56] References Cited

U.S. PATENT DOCUMENTS

| | | | |
|---|---|---|---|
| 3,107,172 | 10/1963 | Baptist et al. | ........................... 106/160 |
| 3,746,688 | 7/1973 | Berkau | .................................. 260/75 T |
| 5,798,440 | 8/1998 | Liddell et al. | ....................... 528/503 X |

FOREIGN PATENT DOCUMENTS

| | | | |
|---|---|---|---|
| 0 046335 | 2/1982 | European Pat. Off. | .......... C12P 7/62 |
| WO 94/02622 | 2/1994 | WIPO | ............................... C12P 7/62 |

OTHER PUBLICATIONS

Database WPI, Section Ch, Week 9042, Derwent Publications Ltd., London, GB: Class A92 AN 90–317488 & JP 02 227 438 (Chuko Kasei Kogyo K), Sep. 10, 1990.

*Primary Examiner*—Fred Teskin
*Attorney, Agent, or Firm*—Gary M. Bond; Arnold, White & Durkee

[57] ABSTRACT

A process of recovering PHA from a suspension which comprises particles of PHA in a liquid which comprises maintaining the suspension at a temperature at which the PHA melts and substantial coalescence of PHA particles occurs thereby at least partly forming a layer of molten PHA and separating the layer of PHA optionally after it cooling to form a solid.

16 Claims, No Drawings

PROCESS OF RECOVERING POLYMERS OF HYDROXYALKANOIC ACIDS

THIS INVENTION relates to the production of polymers of hydroxyalkanoic acid.

It is known, for example from European patents 69497 and 52460 to produce polymers of hydroxyalkanoic acids (PHA) especially polymers and copolymers of hydroxybutyric acid by microbial fermentation. European patent 145233 discloses a process in which microorganisms produced may be treated by heat and reagents in one or more stages to liberate PHA particles contained in them giving a suspension of the particles in an aqueous phase which particles may be separated for example by centrifuging. It may be desirable to resuspend the particles in water in order to carry out further purification.

According to this invention a process of recovering PHA from a suspension which comprises particles of PHA in a liquid comprises maintaining the suspension at a temperature at which the PHA melts and substantial coalescence of PHA particles occurs thereby at least partly forming a layer of molten PHA from the liquid and separating the layer of PHA of the layer from the liquid optionally after cooling to form a solid.

If the process starts from a microbiologically produced PHA suspension, any one or a mixture of the following can be used:
1. whole biomass as produced by fermentation, possibly concentrated or diluted;
2. cell-broken biomass resulting from thermal or mechanical treatment of (1);
3. the product of treating (1) or (2) with a surfactant;
4. the product of treating (1) or (2) with a hydrolase and/or protease enzyme;
5. the product of treating 1, 2, 3 or 4 with an oxidising agent, preferably in presence of a chelator and/or surfactant.

For each of such suspensions there may be a step of concentration or dilution or solubles separation before the melt-separation step. For each of the suspensions made by surfactant treatment in particular, it may be desirable to remove any excess surfactant before the melt-separation step.

The layer of PHA and the layer of the liquid may be formed by permitting the PHA to settle in a molten condition either under normal gravity or under an enhanced gravitational field. Suitably the layers are subject to little or no turbulence during the settling process.

It is preferred that the temperature at which the layers are formed should not greatly exceed the melting point of the PHA. It may for example be up to 25° C. above the said melting point. The temperature and residence time of the PRA should be such that during the period of exposure to the said temperature the molecular weight of the PHA is not reduced below 200,000 and preferably is not reduced below 400,000.

The PHA is preferably a polymer or copolymer of hydroxybutyric acid, for example a copolymer thereof with another hydroxyalkanoic acid preferably having 3 to 10 carbon atoms, for example hydroxyvaleric acid.

Suitably the liquid comprises water.

The layers may be formed in the presence of materials which are soluble in water. Such materials may include the degradation products of non PHA cellular material of microorganisms in which the PHA is formed, reagents used to degrade or solubilise such materials, for example proteases, surfactants or peroxy compounds, for example hydrogen peroxide and decomposition products thereof and nutrients for microorganisms for example carbon nutrients e.g glucose and inorganic nutrients. If desired materials may be added to improve the formation of the layers by for example by reducing the surface activity of other materials which tend to stabilise the suspension.

If a component of the liquid boils at a temperature lower than the melting point of the PHA the process is suitably carried out under pressure in order to avoid turbulence resulting from boiling.

In general temperatures employed in forming the layers are above 100° C., for example 140 to 200° C.; if the liquid comprises water operation under pressure is therefore usually desirable.

In a preferred form of the process a suspension of PHA containing microorganisms in water which may contain nutrients for the microorganisms is contacted with hydrogen peroxide in the presence of a complexing agent which may comprise ethylene diamine tetra acetic acid or ethylene diamine tetra (methylene phosphonic acid) at a temperature sufficient to solubilise non PHA materials and maintained at a temperature sufficient to permit a layer of PHA and an aqueous layer to form and separating the layer of PHA. This form of the invention is advantageous in that it is not necessary as in known processes to introduce added proteases or surfactants and the hydrogen peroxide tends to be reduced to water.

It will be appreciated that the PHA layer may not include all of the PHA present, and some loss of PHA due to this may be accepted or an additional separation stage may be employed to reduce such losses. Separation may be improved using enhanced gravity and suitable centrifuges for separating liquid layers are commercially available and may be used in the invention. It will also be appreciated that the PHA layer may comprise some liquid and other non-PHA matter. If the liquid is water this is removed if the PHA is melt processed and we have found little contamination with non PHA matter, but if desired the PHA layer may be further washed for example by passing it as droplets through fresh water and either repeating the process of this invention to recover a second molten PHA layer or separating solid particles from the washing medium by for example filtering or centrifuging.

The invention may comprise a further step of shearing the separated liquid PHA with surfactant and water and thereby producing a suspension of the PHA in a water/surfactant phase.

The process may be carried out by the steps of:
a) subjecting a suspension which comprises PHA and materials of or derived from living cells in water to a pressure and temperature at which the PHA and water are both in the liquid state until the molten PHA separates as a lower layer;
b) separating the PHA layer from the aqueous layer and mixing it whilst molten with a surfactant and water at a temperature and pressure such that the PHA and water are both in the liquid state thereby forming a fine dispersion of PHA in water and solidifying the PHA by cooling said fine dispersion.

To limit decrease of PHA molecular weight at the relatively high temperatures involved, the separated PHA layer should be cooled or resuspended and cooled as quickly as possible.

Suitable PHAs comprise units of formula I:

$$-O-C_mH_n-CO-$$

where m is in the range 1–13 and n is 2m or (when m is at least 2) 2m−2. Typically $C_mH_n$ contains 2–5 carbon atoms in the polymer chain and the remainder (if any) in a side chain. In very suitable PHAs m is 3 or 4, n is 2m and especially there are units with m=3 and m=4 copolymerized together with respectively a $C_1$ and $C_2$ side chain on the carbon next to oxygen. Particular PHAs contain a preponderance of m=3 units, especially with at least 70 mol % of such units, the balance being units in which m=4. The molecular weight of the PHA is for example over 50000, especially over 100000, up to eg $2 \times 10^6$.

PHA of formula I containing only m=3 units is referred to as PHB; PHA containing m=3 and m=4 units is the co-polymer polyhydroxybutyrate-co-valerate PHBV. PHBV preferably contains 4–20% of m=4 units. The PHA can also be a blend of two or more PHAs differing in the value of m. Correspondingly a mixture of starting suspensions is used.

A particular example contains:
a) PHA consisting essentially of Formula I units in which 2–5 mol % of units have m=4, the rest m=3; and
b) PHA consisting essentially of Formula I units in which 5–30 mol % of units have m=4, the rest m=3. The proportions in such a blend are preferably such as give an average m=4 content in the range 4–20%.

The PHA is preferably the product of a microbiological process in which the microorganism may be wild or mutated or may have had the necessary genetic material introduced into it. Alternatively the necessary genetic material may be harboured by a eucaryote, to effect the microbiological process. Microbiologically produced PHA is chiral (R) and stereospecific.

Examples of suitable microbiological processes are the following:
for Formula I material with m=3 or m=partly 3, partly 4:
  EP-A-69497 (*Alcaligenes eutrophus*);
for Formula I materials with m=3;
  U.S. Pat. No. 4,101,533 (*A. eutrophus*), EP-A-144017 (*A. latus*);
for Formula I material with m=7–13:
  EP-A-0392687 (various *Pseudomonas*).

The microbiological production of the PHA is preferably carried out in two stages:
a) aerobic growth of microorganisms and
b) aerobic fermentation of the resulting organisms in a medium containing a carbon source but deficient in at least one nutrient essential for growth. The deficient nutrient is preferably phosphate.

The surfactant can be cationic, anionic, non-ionic, zwitterionic or contain hydrophilic groups of more than one type. The hydrophobic part of the surfactant preferably contains at least 8, especially 12–20, carbon atoms per hydrophilic group. It may be (almost) wholly aromatic as in sulphonated naphthalenes and naphthyl methanes; or partly aromatic as in alkyl benzene sulphonates or ethoxylates; or wholly aliphatic. Very suitably the surfactant contains a linear alkyl group. If the surfactant is cationic, preferably its hydrophilic part is quaternary ammonium, based for example on tri $C_1$–$C_4$ alkylammonium. If it is anionic, the hydrophilic group is typically sulphate, sulphonate, carboxylate, phosphate or phosphonate. If it is non-ionic, it may be for example an ethoxylate, for example, an alkyl ethoxylate containing 7 to 16 carbon atoms and up to 100 ethoxylate units, or a block copolymer of ethylene oxide and propylene oxide or an alkylphenyl-ethoxylate. Suitable cationic surfactants include, typically as chloride or bromide: dodecyl-, tetradecyl- and cetyl-trimethyl-ammonium, cetyldimethyl-ethylammonium, dodecyl-, tetradecyl- and hexadecyl-benzyldimethyl-ammonium, benzalkonium, benzethonium, methylbenzethonium and cetylpyridinium. Suitable anionics include, typically as sodium salts: dodecyl sulphate, N-lauroylsarcosinate, dioctylsulfo-succinate, cholate, deoxycholate, laurate, myristate, palmitate, and stearate. Suitable non-ionics include sorbitan monopalmitate, alkyl-glucosides and nonyl phenyl-ethoxylates. The surfactants preferred are cetyltrimethylammonium bromide and sodium deoxycholate, dodecyl sulphate, N-lauroylsarcosinate and dioctylsulfo-succinate.

The concentration of PHA in the latex is typically 100 to 600, especially 200 to 500, $g/l^{-1}$. The concentration of surfactant in the shearing step is typically in the range 0.25 to 10, especially 1 to 5% w/w on the polyester component of the mixture.

Typical pressures and temperatures for various PHAs are as follows:

|  | Pressure, |  | Temperature ° C. |
|---|---|---|---|
| PHA homopolymer | $10^6$ Pa | 10 bar | 180 |
| 97:3 B:V | $8 \times 10^5$ | 8 bar | 170 |
| 88:12 B:V | $5.4 \times 10^5$ | 5.4 bar | 155 |
| 79:21 B:V | $3.7 \times 10^5$ Pa | 3.7 bar | 142 |

The high shear mixing may employ any one or more of the following dispersive means for example:
fine nozzle(s) or spinnerets, possibly with vibration, possibly ultrasonic; ultrasonic agitation of a sub-zone or larger body of liquid;
narrow-gap homogenisation such as SILVERSON or ULTRA-TURRAX;
high pressure homogenisation such as APV Manton-Gaulin, Ronnie or Braun & Luebhe; impingement jet homogenisation; plastic milling such as HOBART, BAKER-PERKINS or WERNER-PFLEIDERER; ball-milling or gravel-milling;
paddle agitation, toothed impellor agitation.
Which of these is used depends on temperatures, pressures and PHA viscosity and generally on design convenience.

Conditions in the mixing zone are controlled according to the particle size and particle size distribution of the latex to be produced. Typically the average particle size is in the range 0.05 to 5, especially 0.1 to 1.5, $\mu$m. Average particle sizes of 0.1– 0.4, 0.4–0.6 and 0.8–1.1 $\mu$m appear to be especially suitable for particular applications. The PHA in the particles is preferably at least 96, especially at least 98, % w/w pure. It is preferably low in crystallinity, especially less than 30, particularly less than 20, for example less than 1 percent crystalline as measured by density or wide angle X-ray scattering (WAXS). The percentages are by weight and are believed to represent:

$$\frac{\text{Weight of crystalline PHA}}{\text{total weight of PHA in sample}} \times 100$$

where each particle is either wholly amorphous or crystalline to the full extent practicable.

If desired, the molten PHA may be, before step (d), mixed with a water-soluble liquid that dissolves it at temperatures over 100° C.: this enables it to flow at a temperature below its melting point, and may also make it possible to use less strongly shearing conditions, since the PHA is precipitated from solution in step (d). Among the liquid usable are propylene carbonate, 1.2-propanediol, C4–10 alkanols, C4–10 alkanol acetates, methyl isobutyl ketone and cycloalkanones. Co-solvents such as partly esterified or partly esterified glycols can be introduced at this stage.

The dispersion made according to the invention may be subjected to for example one or more of the following treatments:
concentration or dilution;
removal of excess surfactant, addition of further or different surfactant;
addition of thickener or stabiliser;
addition of pigment or co-solvent.

The dispersion, or latex may be used as such, as for example a coating for paper, polymer films, non-woven boards or foodstuffs. It may alternatively be an intermediate for making dry PHA to be processed as melt or in solution. Such a route may be shorter than conventional routes and, in any event, would permit latex and dry PHA to be made in a single-stream process.

EXAMPLE 1

A strain of *Alcaligenes eutrophus* is grown in batch culture in an aqueous medium on a mixture of glucose and propionic acid under phosphorus limitation to give a culture containing 176 g/l of cells containing 72.2% of a 3-hydroxybutyrate (HB)/3-hydroxyvalerate (HV) copolymer with a hydroxyvalerate content of 21% (the remainder of the polymer being hydroxybutyrate).

A sample of the cells was first heat treated at 150° C. for 80 seconds at pH 6.5. These heat shocked cells were then treated with a proteolytic enzyme (EC 3.4.21.14) at pH 8, 70° C. for 2 hours. At the end of this time the polymer particles were washed free of solubilised cell components by centrifugation and resuspension. The washed particles were resuspended in water, the temperature raised to 80° C. and the pH adjusted to 7. A 350 g/liter hydrogen peroxide solution was added to give a final aqueous phase concentration of 16 g $H_2O_2$ per liter. The temperature and pH conditions were maintained for 12 hours. A sample of the resulting polymer suspension was heated to 140° C. in a sealed thick walled glass tube immersed in an oil bath at 140° C. for 10 minutes. The polymer particles in the heated suspension coalesced and formed on cooling a solid mass of polymer at the base of the tube. After cooling the sample, the polymer plug was removed from the surrounding fluid and analysed for residual polymer impurities.

Analysis of the polymer product indicated that the concentration of residual nitrogen was 550 ppm corresponding to a protein concentration of approximately 3500 ppm. The polymer product was thus considered to be 99.6% pure poly 3-hydroxybutyrate/3-hydroxyvalerate.

Analysis of the polymer product which was separated by centrifugation prior to the heat treatment at 140° C. gave a residual nitrogen concentration of 1530 ppm.

Molecular weight measurements carried out on the polymer indicated that prior to heating to 140° C. the polymer molecular weight was 620,000. After heating to 140° C. for 10 minutes the molecular weight was reduced to 540,000, but the product was still suitable for polymer applications.

EXAMPLE 2

A strain of *Alcaligenes eutrophus* was grown in batch culture in an aqueous medium on a mixture of glucose and propionic acid under phosphorus limitation to give a culture containing 176 g/l of cells containing 72.2% of a 3-hydroxybutyrate (HB) /3-hydroxyvalerate (HV) copolymer with a hydroxyvalerate content of 21% (the remainder of the polymer being hydroxybutyrate).

A sample of the cells was first heat treated at 150° C. for 80 seconds at pH 6.5. These heat shocked cells were then treated with a proteolytic enzyme (EC 3.4.21.14) at pH 8, 70° C. for 2 hours. At the end of this time the pH of the suspension was adjusted to pH 7, the temperature raised to 80° C. and diethylene triamine penta methylene phosphonic acid added to give a final concentration of 6 mM. Hydrogen peroxide solution (350 g/liter) was added to give a final aqueous phase concentration of 50 g/liter. The temperature and pH conditions were maintained for 12 hours.

A sample of the resulting polymer suspension was heated to 140° C. in a sealed thick walled glass tube immersed in an oil bath at 140° C. for 10 minutes.

The polymer particles in the heated suspension coalesced together and formed on cooling a solid mass of polymer at the base of the tube. After cooling the sample, the polymer plug was removed from the surrounding fluid and analysed for residual polymer impurities.

Analysis of the polymer product indicated that the concentration of residual nitrogen was 780 ppm corresponding to a protein concentration of approximately 4800 ppm. The polymer product was thus considered to be 99.5% pure poly-3-hydroxybutyrate/3-hydroxyvalerate.

Analysis of the polymer product separated by centrifugation prior to the heat treatment at 140° C. gave a residual nitrogen concentration of 3300 ppm. Molecular weight measurements carried out on the polymer indicated that prior to heating to 140° C. the polymer molecular weight was 640,000. After heating to 140° C. for 10 minutes the molecular weight was reduced to 560,000 but the product was still suitable for polymer applications.

EXAMPLE 3

The apparatus for this run comprises a screw extruder terminating in a spinneret feeding into a 1-liter pressure vessel including a SILVERSON homogeniser. The pressure vessel is charged with 600 ml of a 3.3% w/w solution of the surfactant sodium dodecyl sulphate, then closed and heated to 150° C. The extruder barrel is heated to 150° C., its screw is started and 400 g of a PHBV (15–20 mol % V) fed to it as powder. Liquid polymer issues from the spinneret and is broken into very fine particles by the homogeniser; the particles remain in suspension as a latex stabilised by the surfactant. The pressure vessel is then cooled and the latex discharged. Instead of or in addition to the SILVERSON homogeniser, the mixture of liquid polymer and surfactant solution could be subjected to ultrasonic agitation or mechanical shear or multiple homogenisation in successive steps or by recirculation.

EXAMPLE 4

A 1-liter pressure vessel equipped with an agitation system is charged with 600 ml of water, 20 g of sodium dodecyl sulphate and 400 g of powdered PHBV (15–20 mol % V). Agitation is set in motion and the vessel is closed and heated to 150° C., sufficient to melt the polymer. After 10 minutes the vessel is allowed to cool, while continuing agitation. The product, a PHBV latex, is discharged.

EXAMPLE 5

Example 2 is repeated, except that, a PHA slurry as described in our copending GB application 9416691.5 is used. That is, a suspension of cells of *Alcaligenes eutrophus* grown on glucose+propionic acid under phosphorus limitation to give at 176 g/l cells containing 72.2% of PHBV (21 mol % V) is heat treated at 150° C. for 80 sec at pH 6.5, treated with a proteolytic enzyme (EC 3.4.21.14) at pH 8, 70° C. for 2 h, then freed of solubilised non-PHA cellular material (NPCM) by centrifugation and resuspension. The washed PHBV particles are resuspended in water and at 80° C., pH 7, treated with hydrogen peroxide 16 g/l for 12 hours.

We claim:

1. A process of recovering polyhydropylakanoate (PHA) from a suspension which comprises particles of PHA in a liquid which comprises maintaining the suspension at a temperature at which the PHA melts and substantial coalescence of PHA particles occurs thereby at least partly forming a layer of molten PHA and separating the layer of PHA optionally after it cools to form a solid.

2. A process as claimed in claim 1 in which the PHA is microbiologically produced.

3. A process as claimed in claims 1 or 2 in which the PHA is a polymer or copolymer of hydroxybutyric acid.

4. A process as claimed in claims 1 or 2 in which the PHA is a copolymer of hydroxybutyric acid and hydroxyvaleric acid.

5. A process as claimed in claim 1 in which the suspension is maintained at a temperature of at most 25° C. above the melting point of the PHA.

6. A process as claimed in claim 1 which is carried out in the presence of materials which are soluble in water.

7. A process as claimed in claim 6 in which the materials soluble in water include at least one of (a) the degradation products of non PHA cellular material of microorganisms in which the PHA has been formed;

(b) the agents used to degrade or solubilise such materials, and/or (c) nutrients for the microorganisms.

8. A process as claimed in claim 1 in which the liquid boils at a temperature lower than the melting point of the PHA and the process is carried out under pressure.

9. A process as claimed in claim 1 in which the temperature is 140–200° C.

10. A process as claimed in claim 1 in which the liquid is water.

11. A process as claimed in claim 1 in which a suspension of PHA containing microorganisms in water is contacted with hydrogen peroxide in the presence of a complexing agent at a temperature sufficient to solubilise non PHA materials and is then maintained at a temperature sufficient to permit a layer of PHA and an aqueous layer to form and separating the layer of PHA.

12. A process as claimed in claims 1 or 11 in which the separation of the layers is carried out using enhanced gravity.

13. A process as claimed in claim 1 in which separated liquid PHA is sheared with a surfactant and water thereby producing a suspension of the PHA in a water/surfactant phase.

14. A process as claimed in claim 11 in which separated liquid PHA is sheared with a surfactant and water thereby producing a suspension of the PHA in a water/surfactant phase.

15. A process as claimed in claim 13 or 14 which comprises the steps of subjecting a suspension which comprises PHA and materials of or derived from living cells in water to a temperature and pressure at which the PHA and water are both in the liquid state until the molten PHA separates as a lower layer separating the PHA layer from the aqueous layer and mixing it whilst molten with a surfactant and water at a high shear rate and at a temperature and pressure such that the PHA and water are both in the liquid state thereby forming a fine dispersion of PHA in water and solidifying the PHA by cooling the said fine dispersion.

16. A process as claimed in claims 1, 5, 8, 9, 11, 13 or 14 in which the molecular weight of the PHA is maintained above 200,000 by restricting the exposure of the PHA to high temperatures.

* * * * *

UNITED STATES PATENT AND TRADEMARK OFFICE
CERTIFICATE OF CORRECTION

PATENT NO.    :   5,952,460
DATED         :   September 14, 1999
INVENTOR(S)   :   John MacDonald Liddell et al.

It is certified that error appears in the above-identified patent and that said Letters Patent is hereby corrected as shown below:

In the Claims:

Column 7, line 6, delete "polyhydropylakanoate" and insert thereof --polyhydroxyalkanoate--.

Signed and Sealed this

Eleventh Day of April, 2000

Attest:

Attesting Officer

Q. TODD DICKINSON

Director of Patents and Trademarks